United States Patent [19]

Schwartz

[11] Patent Number: 5,212,168
[45] Date of Patent: May 18, 1993

[54] METHOD OF AND SOLUTION FOR TREATING GLAUCOMA

[75] Inventor: Bernard Schwartz, Boston, Mass.

[73] Assignee: New England Medical Center Hospital, Inc., Boston, Mass.

[21] Appl. No.: 661,841

[22] Filed: Feb. 26, 1991

[51] Int. Cl.$^5$ .................... A61K 31/56; A61K 31/415
[52] U.S. Cl. .................... 514/179; 514/180; 514/395; 514/913
[58] Field of Search ............... 514/174, 179, 180, 913, 514/395

[56] References Cited

U.S. PATENT DOCUMENTS 4,904,649  2/1990  Schwartz ........................... 514/174

OTHER PUBLICATIONS

The Merck Index Eleventh Edition (1989), pp. 118-119.

Primary Examiner—Frederick E. Waddell
Assistant Examiner—Zohreh A. Fay
Attorney, Agent, or Firm—Lorusso & Loud

[57] ABSTRACT

A method for treating glaucoma consisting of exposing the eye to a corticosteroid and an alpha or a beta adrenergic agent to the eye which acts to decrease ocular pressure. Useful adrenergic agents include beta agonist antagonists, including, for example, epinephrine, dipivalyl epinephrine, betaxolol, levobunolol, timolol, and an alpha adrenergic agonist, including apraclonidine hydrochloride. Useful steroids, which are preferably applied topically, include dexamethasone, prednisolone, cortisone, and triamcinolone. The beta adrenergic agent is administered at a concentration between 10% and 20% of the concentration that the agent is administered in its normal use. The corticosteroid is administered at a concentration between 5% and 10% of the concentration that the corticosteroid is administration in its normal use.

5 Claims, 11 Drawing Sheets

METHOD OF AND SOLUTION FOR TREATING GLAUCOMA

REFERENCE TO RELATED APPLICATION

This application is related to U.S. Pat. No. 4,904,649 by Schwartz, which issued Feb. 27, 1990.

BACKGROUND OF THE INVENTION

This invention is in the field of treatment of eye disease and more particularly in the area of treatments for glaucoma.

Glaucoma is a disease of the eye characterized by increased intraocular pressure. The most common cause of glaucoma is restricted outflow of aqueous fluid from the anterior chamber of the eye through Schlemm's canal, the trabecular meshwork and the aqueous veins, shown in the diagram of the human eye in FIG. 1. Glaucoma, if untreated, can cause excavation and degeneration of the optic disc and nerve fiber bundle damage producing defects in the field of vision and eventually permanent blindness. Roughly two million Americans are afflicted, making glaucoma one of the leading causes of blindness in the United States.

Glaucoma may have a variety of causes, including hereditary predisposition, congenital malformation, disease, injury or adverse drug reaction. For example, angle-closure glaucoma occurs because the outflow of the aqueous humor is mechanically prevented by contact of the iris with the trabecular drainage meshwork and peripheral cornea. Capsular glaucoma occurs in association with the widespread deposition of degenerative substance on the lens capsule, ocular blood vessels, iris and ciliary body. Corticosteroid-induced glaucoma is due to a hereditary predisposition to increased intraocular pressure after local installation of corticosteroid-containing eyedrops. Other types of glaucoma include hypersecretion glaucoma due to the excessive formation of aqueous humor; malignant glaucoma due to forward displacement of the iris and lens obliterating the anterior chamber; and open-angle glaucoma, in which the aqueous humor has free access to the trabecular meshwork.

Glaucoma is treated either surgically or with antiglaucomatous agents. Examples of antiglaucomatous agents include echothiophate iodide, pilocarpine, methazolamide, timolol, and epinephrine, dipivalyl epinephrine and other epinephrine salts. Echothiophate iodide is a long-acting cholinesterase inhibitor for topical use which enhances the effect of endogenously-liberated acetycholine in parasympathetically innervated structures of the eye to increase outflow of the aqueous humor to decrease intraocular pressure. Pilocarpine is a topically applied alkaloid which acts as a parasympathomimetic agent. Methazolamide is a potent inhibitor of the enzyme carbonic anahydrase which is taken orally and acts to lower intraocular pressure by inhibiting carbonic anhydrase in the various tissues of the eye. Timolol maleate is a general beta-adrenergic receptor-blocking agent which is effective in decreasing intraocular pressure. Epinephrine bitartrate, (−)-3,4,-Dihydroxy-alpha [(methylamino) methyl] benzyl alcohol (+) tartrate (1:1) salt, is an adrenergic agent which reduces intraocular pressure by reducing the rate of aqueous formation and increasing the outflow of aqueous humor from the eye. Apraclonidine hydrochloride (available as IPODINE, a trademark of Alcon Laboratories, Forth Worth, TX) is a relatively selective, alpha adrenergic agent which, when instilled into the eye, has the action of reducing intraocular pressure. A more detailed description is given in *The Physicians Desk Reference* (PDR) for Orthomology, 1989, pp 76–77.

Epinephrine is a very effective drug against glaucoma and deserves use as the initial medical treatment of mild cases as well as in addition to other medications when required for control of difficult cases. Clinical studies, reported in *Ocular Pharmacology*, at pages 275–290 by William H. Havener (The C. V. Mosby Co., St. Louis, 1983,) of a number of sympathomimetic compounds showed that a 1% to 2% solution of levo-epinephrine often helps to control glaucoma.

For example, topical application of a 2% solution of levo-epinephrine to 44 glaucomatous eyes caused an average drop in pressure of 13.5 mmHg, ranging from 3 to 38 mmHg. A marked pressure drop was obtained within 1 hour, and pressure continued to fall slightly for 4 hours. A slow rise followed, with a good effect lasting for 12 hours and a slight effect for as long as 24 hours. Eyes most likely to respond well to a 2% solution of levo-epinephrine were those with a coefficient of outflow better than 0.15, the pressures of which were maintained in the upper twenties with miotics. The pressure in most of these eyes could be dropped to the low twenties or below by instillation of a 2% solution of levo-epinephrine twice daily. Although in some instances glaucoma could be controlled by a 2% concentration of levo-epinephrine alone, the best results were obtained when this drug was used in combination with a miotic such as pilocarpine.

It is desirable to use as low a concentration of epinephrine as possible since epinephrine frequently causes side effects such as local allergy and systemic cardiovascular adrenergic responses and it may cause angle-closure glaucoma and aphakic maculopathy. A statistically significant pressure-lowering effect can be demonstrated with epinephrine concentrations as low as 0.5%. However, a substantially greater response occurs with a 1% to 2% solution. Dipivalyl epinephrine is a lipophilic epinephrine derivative and is converted to epinephrine in the ocular tissue. It is reported to have fewer side effects than epinephrine, (William H. Havener, *Ocular Pharmacology* at pages 287–289).

In general, drugs such as steroids are not used in the treatment of glaucoma. Rather, prolonged use of steroids such as dexamethasone sodium phosphate can result in elevated intraocular pressure, damage to the optic nerve, defects in visual acuity and fields of vision, posterior subcapsular cataract formation or secondary ocular infections. Further, viral, bacterial and fungal infections of the cornea may be exacerbated by the topical application of steroids to the eye.

Although the antiglaucomatous agents are generally effective in the treatment of glaucoma, they have both systemic and local side effects which may be serious in combination with other medical treatments such as anesthesia or the systemic use of other drugs. Beta blocker drugs such as timolol, and levobunolol cannot be used with people suffering from asthma or heart problems.

Systemic effects of epinephrine include increased blood pressure, faintness, headaches, and interactions with anesthesia. The side effects of topical epinephrine include burning, slow wound healing, pigment deposition and eyelash loss. Early commercial preparations of levo-epinephrine produced a very severe burning sensation, which was often sufficiently marked to incapacitate the patient for a minute or so and required preliminary use of a local anesthetic in some patients. Presently available preparations still cause tearing, burning and ocular discomfort. Mitosis and migration of corneal epithelial cells is inhibited by epinephrine and the time required for healing of corneal epithelial defects is doubled. Prolonged topical use of levo-epinephrine occasionally causes a local conjunctival allergy and localized conjunctival deposits of pigment. Corneal pigmentation caused by epinephrine is particularly likely to occur in eyes with a damaged epithelium and is enhanced by the use of old and discolored solutions of oxidized epinephrine. Topical epinephrine therapy can also cause plastic artificial eyes and contact lenses to turn black.

The side effects of topical epinephrine therapy are quite annoying. In one series of 50 patients, reported in *Ocular Pharmacology* by William H. Havener at pages 275-290, only 20% could continue epinephrine drops for a four-year period. Reactive hyperemia, irritation, and tearing affected two-thirds of the patients. Headaches affected 5 patients; cardiac palpitations, 4; blurred vision, 10; allergy, 6; and conjunctivial pigmentation, 12.

Adverse reactions reported in association with the use of the alpha adrenergic agonist IOPIDINE Ophthalmic Solution (apraclonidine hydrochloride) in laser surgery are upper lid elevation (1.3%), conjunctival blanching (0.4%) and mydriasis (0.4%). Other adverse events have been observed in investigational studies dosing IOPIDINE Ophthalmic Solution once or twice daily for up to 28 days in nonlaser studies, including, for example, the above mentioned events, ocular burning, discomfort, foreign body sensation, dryness, itching, hypotony, blurred or dimmed vision, allergic response, conjunctival microhemorrhage, in additional to other adverse events including, some in the gastrointestinal, cardiovascular, and central nervous systems. (PDR for Orthomology, 1989, pp. 76-77.)

It is therefore an object of the present invention to provide a method of treatment of glaucoma which is safe, effective, and has a minimum of side effects.

It is a further objective of the present invention to provide a method of treatment of glaucoma which utilizes a minimum of biologically-active compounds.

It is still a further objective of the present invention to provide a method for treatment of glaucoma which produces a decrease in ocular pressure which is of a reasonable duration.

SUMMARY OF THE INVENTION

The present invention is a method for treating glaucoma in humans which consists of administering to the eye two drugs; a corticosteroid and either a beta adrenergic agent, including beta agonists and antagonists, or an alpha adrenergic agonist. The dosage of each drug administered is far less than the normal dosage of these drugs for their primary intended purposes. The dosage of the beta or alpha adrenergic agent is between about 10 and 20% of the normal dosage based upon the drugs as a free base. The dosage of the corticosteroid is between about 5 and 10% of the normal dosage based upon the drug as a free base. The preferred corticosteroid is dexamethasone and the preferred beta adrenergic agent is epinephrine. The treatment results in a significant decrease in intraocular pressure.

In the preferred embodiment, a solution of between about 0.005 and 0.01% dexamethasone is topically applied to the eye followed by topical application of a solution of between about 0.001% and 0.1% epinephrine or between about 0.001% and 0.02% dipivalyl epinephrine. The corticosteroid and beta adrenergic agents are generally administered in acid salt form in order to promote their solubility in the liquid gel vehicle in which drugs are dissolved or admixed. However, it is to be understood that the drugs generally are administered as salts, or the like and that the actual concentration of these forms of the drug is higher than that of the free base depending upon the molecular weight of the actual drug form utilized. The interaction of the two drugs is important in determining the extent and duration of decrease of intraocular pressure to the concentrations of the dexamethasone and epinephrine. The two drugs may be administered in combination or in sequence.

The effectiveness of the combination of dexamethasone and epinephrine is unexpected since both systemic and topical application of dexamethasone or other corticosteroids tend to increase ocular pressure. In addition, it is unexpected that a combination of dexamethasone and timolol produces a synergistic reduction in intraocular pressure. Also unexpected is that lower doses of epinephrine with dexamethasone have a greater effect in lowering ocular pressure than higher doses of epinephrine with dexamethasone. Observations have been made in both rabbits and humans demonstrating the effectiveness of the combination.

In yet another preferred embodiment, a solution of between 0.0005 and 0.01% of dexamethasone, for example, is topically applied to the eye followed by topical application of a solution of between about 0.1% and 0.25% apraclonidine hydrochloride. Here again the two drugs may be administered in combination or in sequence. The effectiveness of this combination is unexpected since both systemic and topical application of dexamethasone or other corticosteroids tend to increase ocular pressure.

DETAILED DESCRIPTION OF THE INVENTION

Figure 1:
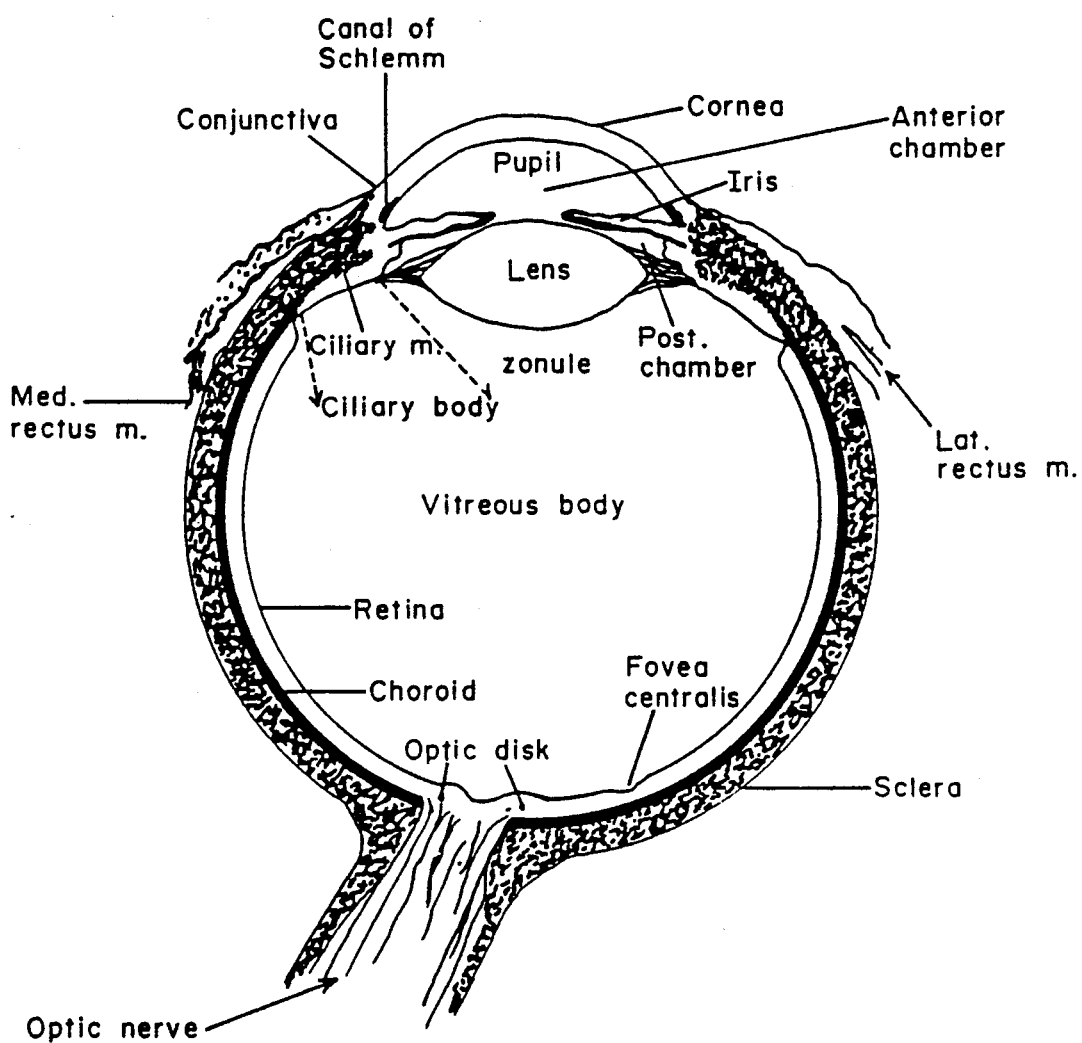
FIG. 1: A cross-sectional view of the right human eye.

The present invention is the treatment of glaucoma with two drugs: a corticosteroid such as dexamethasone and a beta or an alpha adrenergic agent. In accordance with this invention, it has been found unexpectedly that the greatest reduction of intraocular pressure (IOP) is attained when both drugs are administered at far lower concentrations that presently utilized concentrations when the drugs are administered for their presently-known intended use. It has been found that the dosage of the beta and alpha adrenergic agent should be administered at a concentration which is between about 10% and about 20% of the normal concentration dosages. In this concentration dosage, maximum IOP reduction is attained and undesirable side effects of the adrenergic agent are substantially reduced or eliminated. The dosage of the corticosteroid should be administered at a concentration of between about 5% and 10% of the normal concentration dosage. Again, it has been found that in this concentration range the reduction of IOP is maximized and undesirable side effects of the corticosteroid are minimized or eliminated. In addition, it has been found that when employing the concentration of the drugs in accordance with the invention, the effect of reduced IOP is observed for periods of time longer than when employing higher concentration of the drugs.

A number of beta adrenergic agents are useful in the present invention, including epinephrine, dipivalyl epinephrine and other epinephrine salts, and beta antagonists such as timolol, betaxolol, levobunolol, and various combinations of these drugs.

Likewise useful in the present invention is the alpha adrenergic agonist apraclonidine hydrochloride (IOPIDINE).

Epinephrine or its salts such as the bitartrate salt is a standard drug used in the treatment of glaucoma and is normally administered within a concentration range of about 0.5% to 2%. Epinephrine and dipivalyl epinephrine are useful in the management of chronic simple (open-angle) glaucoma, either alone or in combination with miotics such as pilocarpine, carbonic anhydrase inhibitors, or beta receptor blockers such as timolol. When applied in the absence of corticosteroids, in the conventional manner, epinephrine is topically applied as a sterile aqueous solution on an individual basis, ranging from once to twice daily. Dipivalyl epinephrine is conventionally applied as a 0.1% solution. Betaxolol and levobunolol are typically applied as a 0.5% solution. Timolol is applied as a 0.25 or 0.5% solution. Additional beta adrenergic blockers and their normally employed concentrations for application to the eye can be utilized, including cartelol (1% to 2%), befunolol (0.25% to 0.5%), propranolol (0.5% to 1.0%), pindolol (0.5% to 1.0%), metipranolol (0.1%–0.5%), bupranolol (0.05%–0.5%), ACC 9447 (0.2% to 4.0%), atenolol (4.0%), metroprolol (3.0%), nadolol (2.0%), practolol (1.0%) levomoprolol (2.0%), and S32 468 (1.0%); labetolol, celiprolol, cetamolol, and arotinolol (for which no concentrations are presently available).

IOPIDINE Ophthalmic Solution contains apraclonidine hydrochloride, an alpha adrenergic agonist, in a sterile isotonic solution for topical application to the eye. Apraclonidine hydrochloride is a white to off-white powder and is highly soluble in water. When instilled into the eye, IOPIDINE has the action of reducing intraocular pressure. This drug is typically administered within a concentration range of 1.0% when used alone. In the present invention, the concentration range is about 0.1% to 0.25%.

In the present invention, these lower concentrations are used due to the enhancing effect of the corticosteroid. This has the advantage of decreasing the incidence of severity of side effects due to the adrenergic agent.

Examples of corticosteroids which are useful in the present invention and their normally employed concentrations for application to the eye include dexamethasone (0.1%), prednisolone (1.0%) hydrocortisone (0.5%), cortisone (2.5%), fluoromethalone (0.1%), betamethasone (0.1%), methyl prednisolone 80 mg/ml (injection), triamcinolone (0.1% or 40 mg/ml (injection), and their physiologically acceptable salts.

Dexamethasone sodium phosphate and other corticosteroids are conventionally used for the treatment of steroid-responsive inflammatory conditions such as allergic conjunctivitis, superficial punctuate keratitis, herpes Zoster keratitis, corneal injury from chemical or thermal burns, and in other situations where an inflammatory response has been incited by mechanical or immunological agents. In general, one or two drops of a dexamethasone phosphate solution are topically applied to the eye between three and four times a day up to once every hour, depending on the treatment required. Prolonged use at presently employed normal concentration ranges must be avoided as the dexamethasone causes increased ocular pressure over time. People taking systemic corticosteroids frequently also exhibit increased ocular pressures. In the present invention, the dosage of the corticosteroid is individually adjusted into the lower concentration range as necessary to produce the desired enhancement of pressure decrease, due to the adrenergic agent, which is also of sufficient duration. In general, very small concentrations of corticosteroids will be required.

Medications are routinely applied to the eye by means of a dropper. Variations in the actual amount delivered to the eye will vary somewhat according to the shape and size of the dropper and the skill of the person administering the drops. Administration of the drugs also can be effected topically in an ointment, orally, intraveneously, intramuscularly, transdermally, by subconjunctial injection, sub-Tenon's, intraocular injection, retrobulbar injection or by iontophoresis.

In combination with epinephrine, dexamethasone has been demonstrated to enhance the effectiveness of epinephrine in decreasingly intraocular pressure, allowing the use of lower concentrations of epinephrine to achieve the same decrease in pressure. Since the mechanism by which this occurs involves an enhancement in the number, binding affinity, or some other function of the adrenergic receptors by the corticosteroids, other corticosteroids may be used with other adrenergic agents to produce the same result. The advantages are immediately noticeable, most significant being the decrease in both systemic and local side effects due to the adrenergic agent.

This invention is further illustrated by the following non-limiting examples. In a first group of examples, rabbit eyes were treated with a combination of dexamethasone and epinephrine to decrease ocular pressure. Rabbits are the standard model for testing the reaction of human eyes to drugs or other foreign agents. In a second group of examples, clinical observations were made on patients suffering from elevated ocular pressures.

EXAMPLE 1

Enhanced Ocular Hypotensive Response to Epinephrine in Rabbits with Prior Dexamethasone Treatment-Epinephrine Dose Response.

MATERIALS AND METHODS

Male New Zealand albino rabbits were used, weighing 2.0 to 2.5 Kg each.

The rabbits were acclimated to their new surroundings, to frequent handling, and to the measurement of intraocular pressure (IOP). Serial IOP measurements were taken daily for four to seven days before the experiment began. The experiment was begun only when these daily pressure readings were stable. After a single topical application of 0.5% proparacaine (Alcaine) for corneal anesthesia, IOP was measured with a Digilab (Cambridge, Mass.) pneumotonometer; the readings were recorded on paper. The pneumotonometer was calibrated before use on the day of the study.

A day before the experiment, the rabbits were divided into four groups so that the mean ocular pressures of each group were within ±1 mmHg of each other. The four groups consisted of a control group that received saline (0.9% sodium chloride) drops in both eyes; an epinephrine group that was treated with saline drops followed by epinephrine bitartrate drops; a dexamethasone/epinephrine group that received pretreatment with dexamethasone phosphate drops followed by epinephrine drops; the fourth group received only dexamethasone in both eyes and served as a second control group. The rabbits' eyes were pretreated with five applications of a single drop of saline drops or with dexamethasone, depending on the protocol of the assigned group.

Baseline IOP was measured at about 8:00 AM, 8:30 AM and 9:00 AM. Saline or 0.07% dexamethasone (0.1% dexamethasone phosphate) drops were administered about every 15 minutes from 9:15 to 10:15 AM, for a total of five applications. IOP was measured again at 10:30 AM. At 10:45 AM the animals were treated with one drop of either saline or epinephrine bitartrate, and IOP was subsequently measured about every 30 minutes unitl 3:00 PM. All pressures taken at any time were measured only once.

Concentrations of epinephrine (bitartrate) used were 1.10% (2%), 0.27% (0.5%), 0.05% (0.1%), 0.005% (0.01%) and 0.0005% (0.001%). Dexamethasone was always used at 0.07% (0.1% dexamethasone phosphate) concentration. Both the epinephrine bitartrate and dexamethasone phosphate solutions were prepared at the time of each experiment by dissolving the solute in 0.9% saline solution.

Prelimninary studies showed that dexamethasone alone compared to saline had no effect on IOP. The dexamethasone group was therefore dropped from subsequent studies.

For each experiment, there were three animals in each saline group, epinephrine group and dexamethasone/epinephrine group. Each experiment was then carried out several times for all the epinephrine concentrations except one (Table 1).

For statistical analysis the Kruskal-Wallis (multiple comparison test) was used to detect differences between the groups at each time of measurement. When this test demonstrated a significasnt difference between two of the three test groups ($p < 0.05$), the Mann-Whitney U test was used to detect statistically significant differences between the two groups. The statistical analysis of the right and left eyes was performed separately. Only two-tailed tests were used to determine significance.

Results

Figure 2:
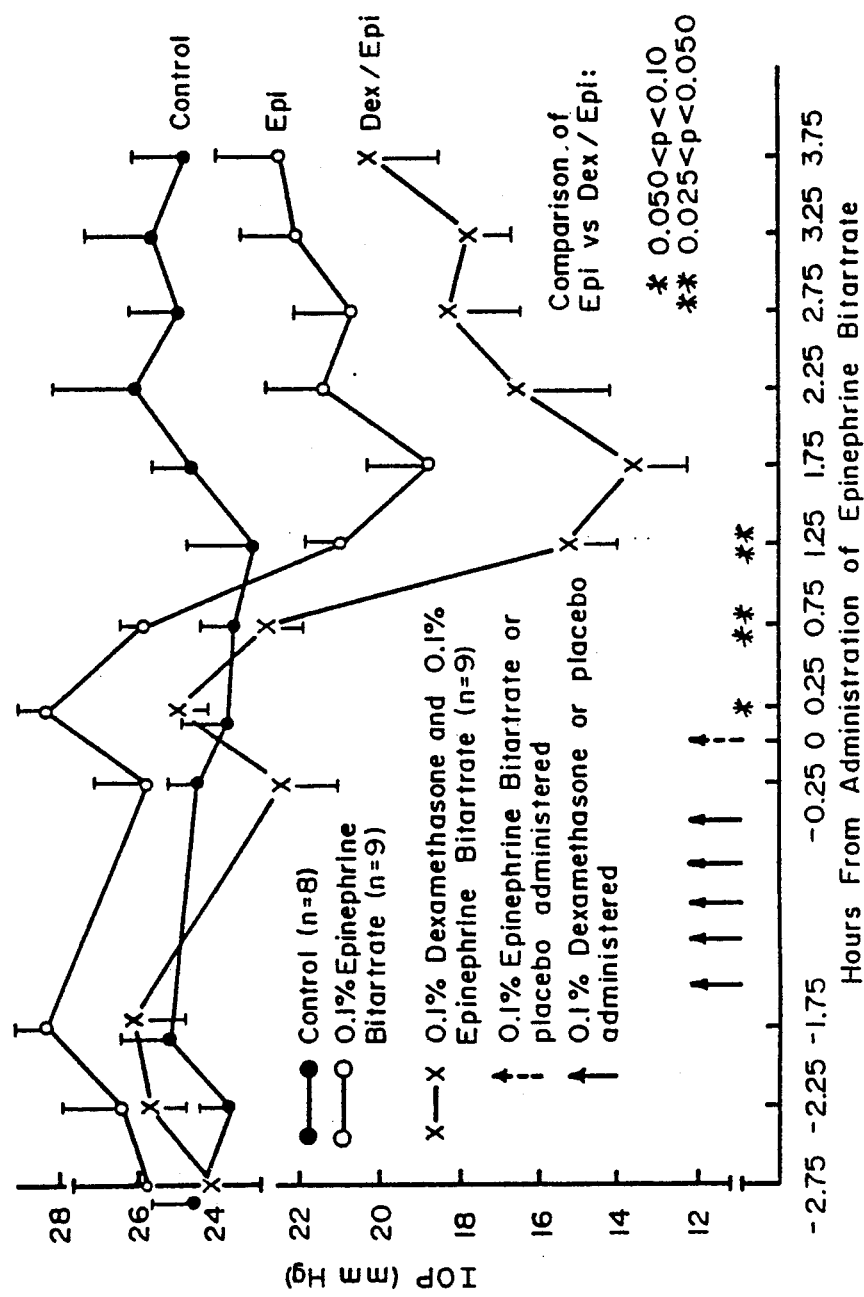
FIG. 2: Change in mean pressure ± standard error of the means (SEM) over time for the right eyes for the three groups of rabbits using epinephrine concentration 0.027% (0.05% epinephrine bitartrate) and dexamethasone concentration 0.07% (0.1% dexamethasone phosphate). Vertical bars are the standard errors of the mean. Asterisks indicate the times at which the epinephrine/dexamethasone group was significantly different from the epinephrine group. The arrows indicate time of administration of the drugs.

A typical plot of the changes in mean pressures over time for the three groups of rabbits (epinephrine alone, dexamethasone and epinephrine, saline) is shown in FIG. 2. The three groups did not demonstrate any significant change in IOP in the four baseline pressure measurements except for the 1.1% epinephrine group, which had a significant change 15 minutes before the administration of epinephrine (Table 1). Approximately 15 minutes after the administration of epinephrine, both the epinephrine group and the epinephrine/dexamethasone group showed a significant drop in pressure, with most of the significant differences occurring 45 minutes after the administration of the epinephrine drops (Table 1). However, the drop in IOP for the epinephrine/dexamethasone group is larger than the epinephrine group. With time, both groups returned to about baseline levels at the end of the period of study. The pressure measurements of the saline groups were stable throughout the seven hours of the experiment.

Table 1 shows the number of animals used for the various epinephrine concentrations as well as the p-values and the mean IOP for those concentrations in which the dexamethasone/epinephrine and the epinephrine group showed significant and borderline differences. In those concentrations of epinephrine where no significant differences were observed, comparable data at 45 minutes was included.

The largest difference in mean IOP between the epinephrine and epinephrine/dexamethasone groups was 4.9 mmHg, which occured 45 minutes after the instillation of 0.005% epinephrine drops. At this concentration of epinephrine, the decrease in mean IOP compared to the saline group was 9.5 mmHg for the epinephrine/dexamethasone group, occurring at 45 minutes after the instillation of epinephrine drops. The mean decrease in IOP in the epinephrine group for the same concentration, compared to the saline group, was 4.6 mmHg.

Figure 3:
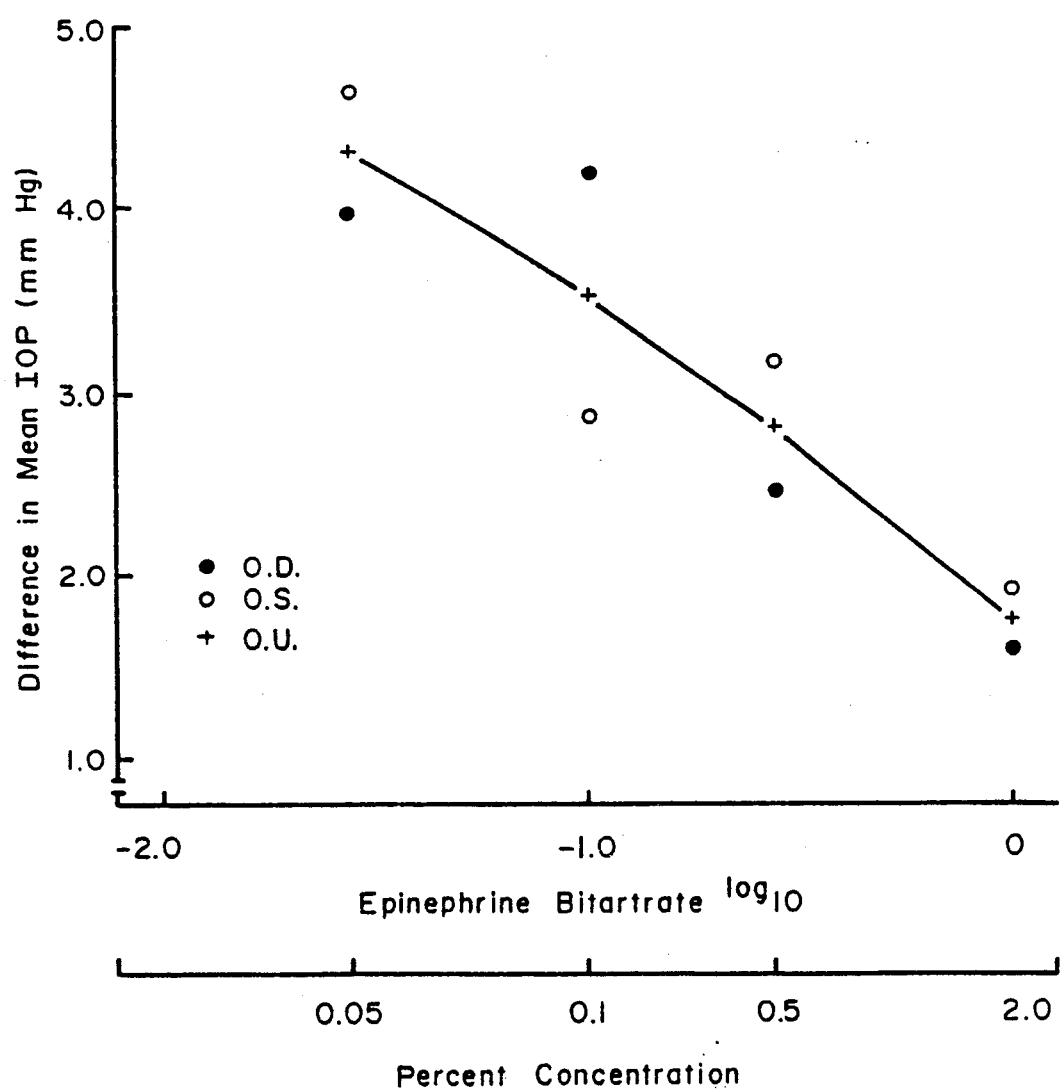
FIG. 3: Epinephrine dose response curve. Difference of mean IOP (vertical bars-SEM) for average IOP for both eyes for the dexamethasone/epinephrine group minus the epinephrine group at 45 minutes after the administration of epinephrine drops.

FIG. 3 plots the dose response curve for epinephrine at 45 minutes after the administration of epinephrine. This is the time when the most significant differences occurred (Table 1). The response is the amount of mmHg decrease in IOP in the dexamethasone/epinephrine group minus the epinephrine group when both eyes are averged together. The dose response curve shows that the larger the dose of epinephrine, the less is the response. The maximum difference that occurred at 45 minutes after the administration of epinephrine was mean=5.8 mmHg at 0.0005% free base epinephrine concentration.

Figure 4:
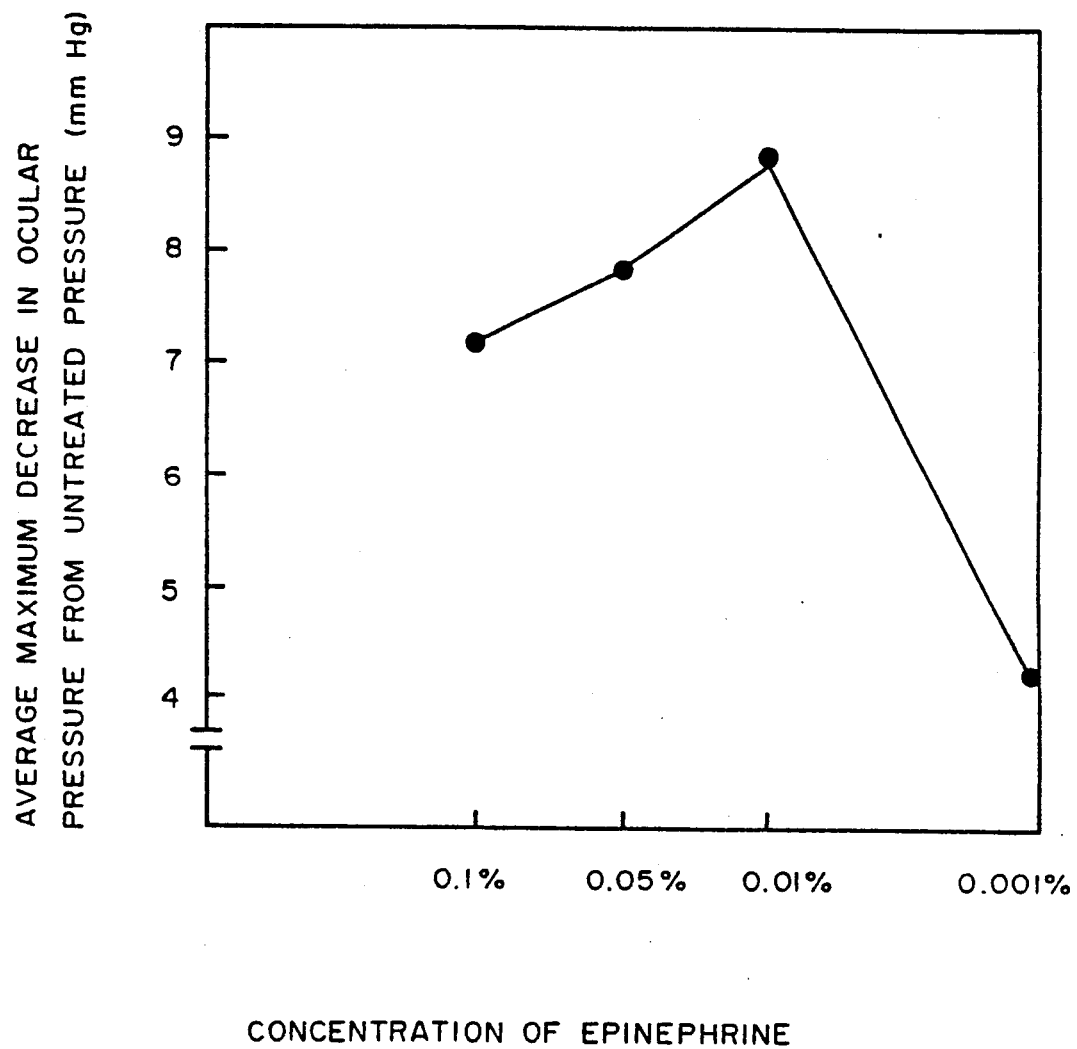
FIG. 4: Difference in time (min) (vertical bars-SEM) taken for IOP to return to pretreatment baseline. Mean IOP of average of both eyes of dexamethasone/epinephrine group minus the epinephrine group (free base) concentrations when both eyes are averaged.

FIG. 4 plots the duration of the effect of dexamethasone pretreatment as the time taken for the dexamethasone/epinephrine group minus the time taken for the epinephrine group to return to pretreatment baseline levels for the various epinephrine concentrations when both eyes are averaged together. As with the dose response curve, the larger the epinephrine concentration, the less time it took for the IOP to return to baseline level. The largest mean difference in duration was 97 minutes at the 0.0005% epinephrine concentration.

In this study, pretreatment with dexamethasone resulted in a further mean decrease of 4.9 mmHg from baseline in 0.005% epinephrine (0.01% epinephrine bitartrate) and 5.8 mmHg from baseline 0.0005% epinephrine (0.001% epinephrine bitartrate).

This study also demonstrated that the reduction in IOP is dose dependent on epinephrine; however, the larger the epinephrine concentration, the smaller the response (FIG. 3). A similar inverse relationship to dose was shown for the duration taken for the decrease in IOP to return to baseline level.

EXAMPLE 2

Demethasone Dose Response for the Enhanced Ocular Hypotensive Response to Epinephrine in Rabbits with Prior Dexamethasone Treatment Materials And Methods Male New Zealand albino rabbits weighing 2.0 to 2.5 Kg each were used. The rabbits were acclimated to their new surroundings, to frequent handling and measurement of intraocular pressure (IOP). Serial IOP measurements were taken daily for four to seven days before the experiment began. The experiment was begun only when these daily pressure readings appeared stable. After a single topical application of 0.5% proparacaine (Alcaine) for corneal anesthesia, IOP was measured with a Digilab (Cambridge, Mass.) pneumotonometer; the pressure readings were recorded on paper. The pneumotonometer was calibrated before use on the day of each study.

The day before the experiment, rabbits were randomized into three groups so that the mean ocular pressure between the three groups was within ±1 mmHg. The three groups were: a control group which received saline (0.9% sodium chloride) drops in both eyes; an epinephrine group that was treated with saline followed by epinephrine bitartrate drops and a dexamethasone/epinephrine group that received pretreatment with dexamethasone phosphate drops followed by epinephrine drops.

TABLE 1

Comparison of saline, epinephrine and dexamethasone/epinephrine groups for the various epinephrine concentrations.

| Epinephrine conc. (Free Base) | Eye OD/OS | Time* (Min) | Saline group Mean ± SEM (n**) | Epinephrine group Mean ± SEM (n**) | Dexamethasone/ Epinephrine*** Mean ± SEM (n**) | p value**** |
|---|---|---|---|---|---|---|
| 1.1% | OS | −15 | 23.7 ± 1.3 (11) | 25.2 ± 0.8 (12) | 20.5 ± 1.5 (12) | 0.03 |
|  | OD | 45 | 26.2 ± 1.1 (11) | 23.2 ± 0.9 (12) | 19.2 ± 0.9 (12) | 0.02 |
|  | OD | 45 | 24.6 ± 1.3 (11) | 25.6 ± 1.2 (12) | 24.5 ± 1.0 (12) | 0.02 |
| 0.27% | OD | 45 | 25.7 ± 1.4 (9) | 27.0 ± 2.2 (9) | 24.5 ± 2.4 (9) | NS |
| 0.05% | OD | 45 | 24.4 ± 1.2 (12) | 25.8 ± 0.6 (12) | 21.6 ± 1.2 (12) | 0.01 |
|  | OD | 75 | 25.2 ± 1.0 (12) | 19.6 ± 0.8 (12) | 15.6 ± 1.1 (12) | 0.01 |
|  | OS | 45 | 23.6 ± 1.0 (12) | 25.9 ± 0.6 (12) | 23.0 ± 0.7 (12) | 0.01 |
| 0.027% | OD | 15 | 24.1 ± 1.5 (9) | 23.4 ± 0.9 (9) | 19.5 ± 1.1 (9) | 0.03 |
|  | OS | 45 | 22.8 ± 1.1 (9) | 20.1 ± 0.6 (9) | 15.5 ± 1.1 (9) | 0.02 |
|  | OS | 15 | 20.7 ± 1.4 (9) | 23.3 ± 1.1 (9) | 18.7 ± 1.5 (9) | 0.02 |
|  | OS | 45 | 20.6 ± 1.5 (9) | 18.4 ± 0.9 (9) | 15.4 ± 1.1 (9) | 0.05 |
| 0.005% | OD | 45 | 20.1 ± 1.3 (3) | 15.5 ± 2.5 (3) | 10.6 ± 2.6 (3) | 0.07 |
| 0.0005% | OD | 45 | 21.2 ± 2.3 (6) | 21.5 ± 2/1 (6) | 15.6 ± 1.9 (6) | NS |

*Time is calculated in relation to the administration of epinephrine.
**n = Number of animals in each group.
***Dexamethasone concentration (free base) is constant at 0.07%.
****p value from Mann-Whitney U test-comparison of epinephrine group with Dexamethasone/epinephrine group.

On the day of the experiment baseline IOP was measured at about 8:00 AM, 8:20 AM, and 9:00 AM. Saline or dexamethasone drops were administered from 9:15 AM to 10:15 AM at about 15 minute intervals for a total of five applications. IOP was measured again at 10:30 AM. At 10:45 AM the animals were treated with one drop of either saline or epinephrine topically, and IOP was subsequently measured about every 30 minutes until 3:00 PM. Throughout the experiment pressures were measured only once at each time interval.

Concentrations of dexamethasone (phosphate) used were 0.07% (0.1%), 0.007% (0.01%), 0.0007% (0.001%) and 0.0004% (0.0005%). Epinephrine was always used at a free base concentration of 0.005% (0.01% epinephrine bitartrate). Both the dexamethasone phosphate and the epinephrine bitartrate solutions were prepared at the time of each experiment by dissolving the solution in 0.9% saline solution.

For each experiment there were three animals in the control group, the epinephrine group, and the epinephrine/dexamethasone group. Each experiment was carried out once for all dexamethasone concentrations except one (Table 2).

For statistical analysis the Kruskal-Wallis (multiple comparison) test was used to detect differences in IOP between the groups at each time of measurement. When this test demonstrated a significant difference between two of the three groups ($p < 0.05$), the Mann-Whitney U test was used to detect statistically significant differences between the two groups. The statistical analysis of the right and left eyes was performed separately. Only two-tailed tests were used to determine significance.

Results

Figure 5:
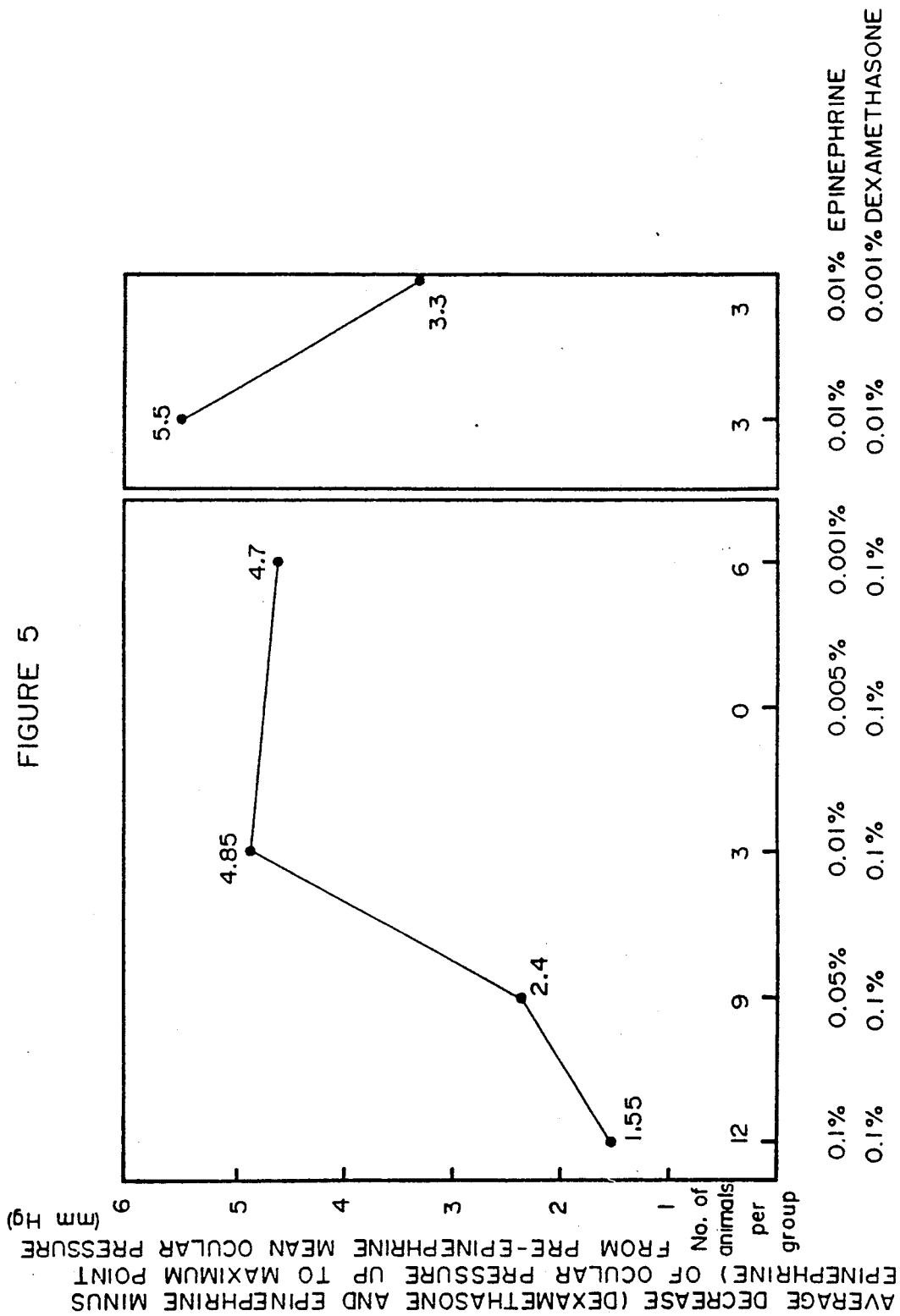
FIG. 5: Change in mean pressure ± standard error of the mean (SEM) over time for the left eye for the three groups of rabbits, using 0.005% epinephrine concentration (0.1% epinephrine bitartrate) and 0.0007% dexamethasone concentration (0.001% dexamethasone phosphate). Vertical bars are the standard errors of the mean. Asterisks indicate the times at which the epinephrine/dexamethasone group was significantly different from the epinephrine group. The arrows indicate time of administration of the drugs.

A typical plot of the changes in mean pressures over time for the three groups (epinephrine alone, dexamethasone and epinephrine, saline) is shown in FIG. 5. The three groups did not demonstrate any significant differences in IOP at the times of the four baseline pressure measurements. Approximately 45 minutes after the administration of epinephrine, both the epinephrine group and the dexamethasone/epinephrine group showed a drop in IOP compared to the saline group. However, only the epinephrine/dexamethasone group is significantly different from the saline group. Both groups then returned to about baseline levels within 4-5 hours at the end of the period of study. The saline group had stable IOP measurements throughout the seven hours of the experiment.

Table 2 shows the number of animals used for the various dexamethasone concentrations as well as the p values and the mean IOP for these concentrations in which the dexamethasone/epinephrine groups showed a significant and borderline difference from the epinephrine group. The 0.0004% dexamethasone group showed no significant difference.

The decrease in mean IOP from the mean saline group level for the dexamethasone/epinephrine group was: 8.3 mmHg, which occured 45 minutes after the administration of epinephrine when using 0.0007% concentration. This was the concentration of dexamethasone and the time that produced the largest difference in mean IOP (6.6 mmHg) between the epinephrine group and the dexamethasone/epinephrine group.

Figure 6:
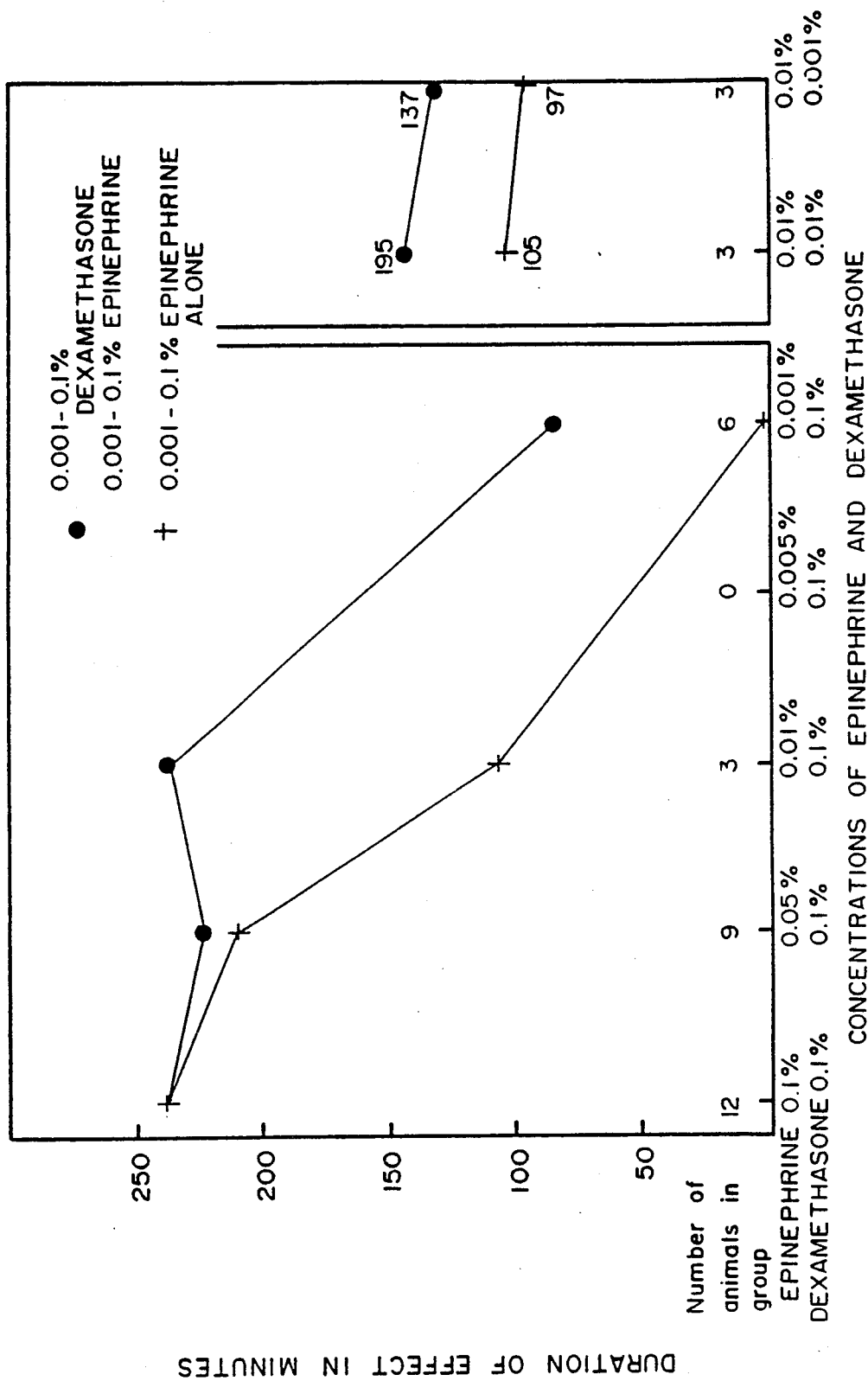
FIG. 6: Dexamethasone Dose Response Curve. Difference of mean IOP (vertical bars-SEM), for the average IOP of both eyes for the Dexamethasone/epinephrine group minus the epinephrine group at 45 minutes after the administration of epinephrine drops.

FIG. 6 plots the dose response curve for dexamethasone 45 minutes after the administration of epinephrine drops. At this time the most significant differences occurred between the epinephrine group and the dexamethasone/epinephrine group (Table 2). The response is the amount of decrease in IOP (mmHg) in the dexamethasone/epinephrine group minus the epinephrine group when both eyes are averaged together. The dose response curve shows that the larger the dexamethasone concentration, the greater the response. The mean maximum difference 45 minutes after the administration of epinephrine was 6.3 mmHg at the 0.007% dexamethasone concentration.

Figure 7:
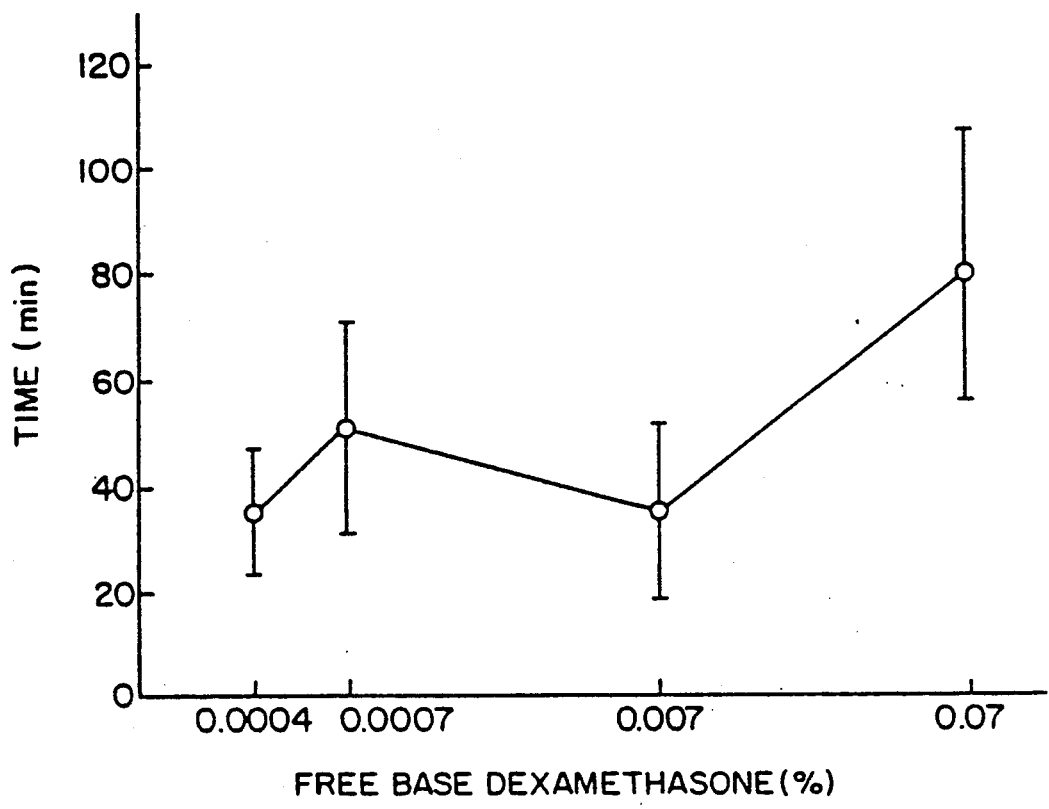
FIG. 7: Difference in duration (vertical bars-SEM) taken for IOP to return to pretreatment baseline. Mean IOP of dexamethasone/epinephrine group minus epinephrine group for the average IOP of both eyes, at various dexamethasone (free base) concentrations.

FIG. 7 plots the duration of the effect of dexamethasone pretreatment as the time taken for the dexamethasone/epinephrine minus the time taken for the epinephrine group to return to pretreatment baseline level for the various epinephrine concentrations when averaging both eyes together. As with the dose response curve, the larger the dexamethasone concentration, the longer it took for the IOP to return to baseline level. The longest mean difference in duraton was 80 minutes at 0.07% dexamethasone concentration.

The dexamethasone dose response curve shows that the larger the concentration of dexamethasone, the larger is the response (FIG. 5) and the longer the duration taken for IOP to return to baseline level (FIG. 6). Unlike epinephrine, dexamethasone shows the typical pattern of dose dependent response.

TABLE 2

Comparison of saline, epinephrine, and dexamethasone/epinephrine groups by the various dexamethasone concentrations.

| Epinephrine conc. (Free Base) | Eye OD/OS | Time* (Min) | Saline group Mean ± SEM (n**) | Epinephrine group Mean ± SEM (n**) | Dexamethasone/ Epinephrine*** Mean ± SEM (n**) | p value**** |
|---|---|---|---|---|---|---|
| 0.07% | OD | 45 | 20.1 ± 1.3 (3) | 15.5 ± 2.5 (3) | 10.6 ± 2.6 (3) | 0.0656 |
| 0.007% | OS | 45 | 24.4 ± 2.2 (3) | 22.4 ± 1.9 (3) | 16.7 ± 2.3 (3) | 0.0453 |
| 0.0007% | OD | 45 | 26.4 ± 1.2 (6) | 24.7 ± 2.3 (6) | 18.1 ± 1.9 (6) | 0.0547 |
|  | OS | 75 | 25.1 ± 0.4 (6) | 23.1 ± 2.3 (6) | 16.7 ± 1.4 (6) | 0.0542 |
| 0.0004% | OD | 45 | 31.0 ± 1.0 (3) | 23.3 ± 3.3 (3) | 25.6 ± 3.7 (3) | NS |

*Time is calculated following the administration of epinephrine.
**n = Number of animals in each group.
***Epinephrine concentration (free base) is constant at 0.005%
****p Value from Mann-Whitney U test - comparison of the epinephrine group with dexamethasone/epinephrine group.

A low concentration of dexamethasone (0.0007%) can significantly enhance the reduction of IOP. This hypotensive effect lasts longer than if the eyes were treated with epinephrine alone.

EXAMPLE 3

Enhanced Ocular Hypotensive Response to Epinephrine with Prior Dexamethasone Treatment—an Acute Clinical Trial in Ocular Hyptonsives

Methods

Patients with untreated ocular hypertension were selected from the outpatient service of the Ophthalmology Department of the New England Medical Center. Informed consent was obtained. The experimental protocol and consent forms were approved by the Human Investigation Review Committee. The diagnosis of ocular hypertension was made by two independent measurements of ocular pressure of 21 mmHg or greater with the Goldmann applanation tomoneter. These patients had complete ocular examinations to determine that no other significant ocular pathology was present. Normal visual fields were present as tested by the Octupus perimeter with programs 7 and 31. The presence of open angles was observed on slit lamp goniscopy. The optic disc may or may not have had changes suggestive of glaucoma.

On the day of the study, two baseline IOP measurements were taken 10 minutes apart in each eye between 8:00 and 9:00 AM. The study drugs were then administered five minutes apart in the following manner: one eye received three drops of 0.01% dexamethasone phosphate (Decadron phosphate, Merck, Sharp and Dohme, equivalent to 0.007% dexamethasone) diluted with artificial tears (Lacril, Allergan, hydroxpropy methycellulose with 0.5% chlorobutanol) followed by one drop of 0.1% epinephrine (Epifrin, Allergan, equivalent to 0.08% of epinephrine free base). The other eye received three drops of artificial tears plus one drop of 0.1% epinephrine hydrochloride. After drug administration, ocular pressures were taken every twenty minutes for two hours.

Dexamethasone phosphate and artificial tear drops were prepared by the hospital pharmacist who placed each in identical containers labeled with codes. The pharmacist prepared a random series for the choice of eye for dexamethasone or artificial tears. The code was broken at the end of the series.

At each time of measurement of pressures the paired test was used to determine the significance of the differences in IOP. Spearman correlations ($r$s) were used to test the relationship to age, and the chi square test was used to test the influence of sex, race and iris color. Two tailed tests were used to define significance.

Results

Patient characteristics were as follows: age ranged from 37 to 81; the average age was 56 years. There were 6 males and 6 females, 2 blacks and 10 whites. Three patients had blue irises, the rest had brown. Two had diabetes mellitus and took insulin. Two had systemic hypertension; one took hydralazine and the other hydrochlorothiazide. One was treated for fluid retention with hydrochlorothiazide. Dexamethasone was given to the left eye seven times and to the right eye five times.

Figure 8:
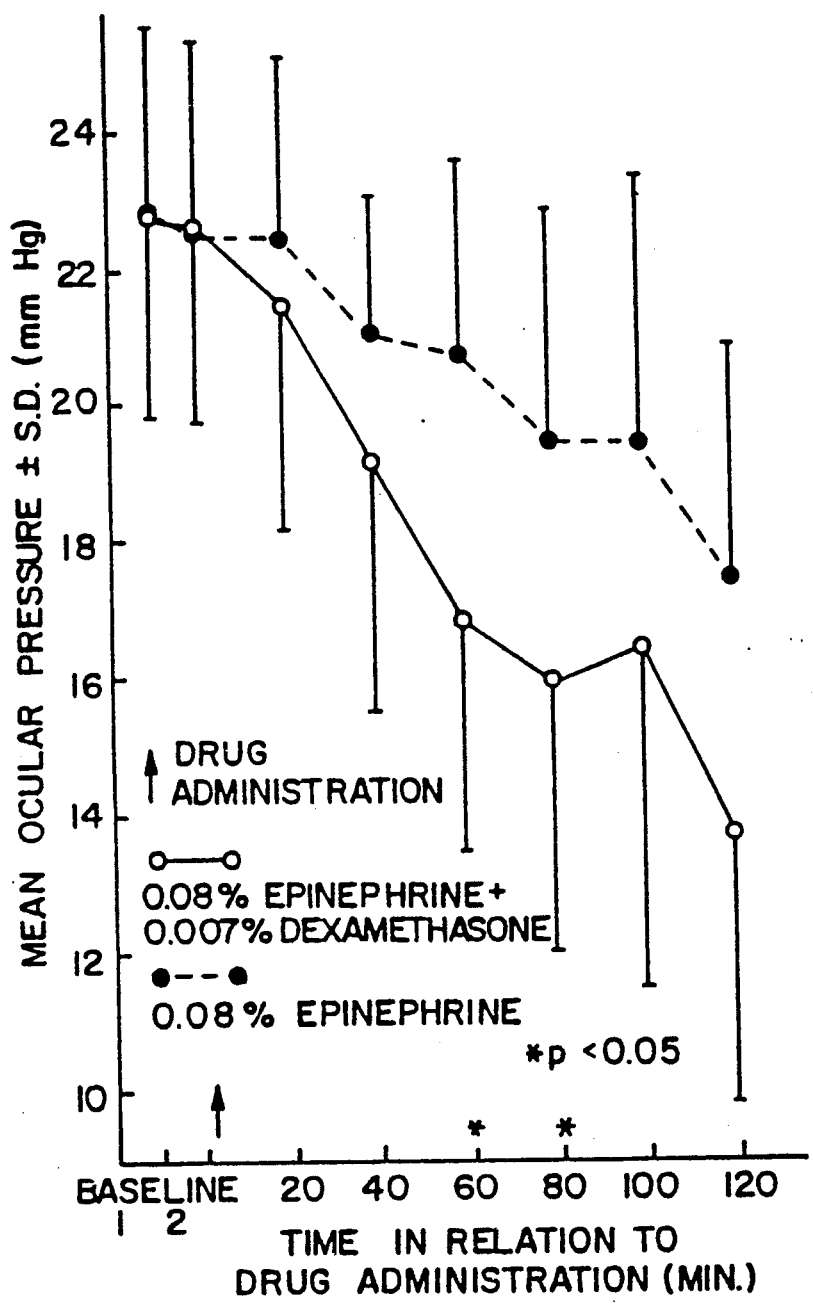
FIG. 8: Epinephrine-dexamethasone response vs. epinephrine: 0.08% epinephrine base ±0.007% dexamethasone. Points represent the mean ocular pressure of all eyes (right or left) either pretreated or not pretreated with dexamethasone. The vertical bars represent standard deviation from the mean. Arrow represents time of epinephrine administration. The asterisks represent time intervals where the intraocular pressure (IOP) differences are significant ($p < 0.05$).

There were no significant differences between the eyes prior to drug administration. (Table 3). Ten of twelve ocular hypertensives showed a greater decrease in IOP in eyes pretreated with dexamethasone compared to eyes treated with epinephrine alone. The mean pressure at each time interval is shown in FIG. 8. Significant differences in IOP were first observed 60 minutes after drugs were given (p=0.006) and was still present at 80 minutes (p=0.04) (Table 3) with the eye receiving the dexamethasone plus epinephrine having lower means than the eye receiving epinephrine alone.

The mean maximum decrease in IOP from baseline was 9.0 mmHg in eyes pretreated with dexamethasone compared to 5.2 mmHg in eyes treated only with epinephrine (Table 3). The mean maximum significant decrease between the eyes pretreated and not pretreated with dexamethasone in these twelve patients was 3.9 mmHg, 60 minutes following epinephrine administration. Two of twelve patients showed no discernible IOP lowering difference. In the ten patients in whom there was a difference, all had a mean maximum difference ≧4.0 mmHg. Of these, four had a mean maximum difference ≧6.0 mmHg. In those patients who showed an effect, the duration of the effect was at least 90 minutes.

The only factor that the two non-responders demonstrated that differentiated them from the responders was that they were the oldest patients in the series (ages 77 and 81).

Spearman correlations of the differences between eyes versus age at 60 minutes showed a significant influence of age (n=12, $r$s=0.63, p=0.03). Greater age was associated with less IOP lowering effects. Sex, race and iris color as tested by the chi square method were not found to be significant factors in this sample.

TABLE 3

Comparison of Ocular Pressures of Epinephrine Treated Eye with Epinephrine plus Dexamethasone Treated Eye

| Times in relation to drug administration (min) | Ocular Pressure (mmHg) | | Paired t Test P |
|---|---|---|---|
| | Epinephrine Alone Mean ± SD (No.) | Epinephrine plus Dexamethasone Mean ± SD (No.) | |
| Baseline 1 | 22.9 ± 2.6 (12) | 22.8 ± 2.8 (12) | 0.78 |
| Baseline 2 | 22.5 ± 2.7 (11) | 22.7 ± 2.8 (11) | 0.91 |
| 20 | 22.5 ± 2.5 (12) | 21.5 ± 3.3 (12) | 0.43 |
| 40 | 21.2 ± 1.9 (12) | 19.2 ± 3.6 (12) | 0.10 |
| 60 | 20.8 ± 2.7 (12) | 16.9 ± 3.4 (12) | 0.006 |
| 80 | 19.5 ± 3.4 (11) | 16.0 ± 3.9 (11) | 0.04 |
| 100 | 19.5 ± 3.9 (7) | 16.5 ± 4.9 (7) | 0.24 |
| 120 | 17.5 ± 4.4 (4) | 13.7 ± 4.0 (4) | 0.26 |

EXAMPLE 4

Enhanced Ocular Hypotensive Response to Timolol in Rabbits with Prior Dexamethasone Treatment Nine male New Zealand Albino rabbits weighing 2.0–2.5 Kg. each were received in the animal quarters at two-week intervals. The first week was used to get the rabbits acclimated and adapted to applanation tonometry. On the day prior to the start of the experiment, the rabbits were divided into three groups, with each group having the same mean intraocular pressure (IOP), within ±1 mmHg, as based on the average of their previous four days pressure readings. The groups were the timolol group, the timolol/dexamethasone group, and the saline control group. On the morning of the study IOP was measured between 0800 and 0900 hours at thirty minute intervals, in all animals. Between 0900 and 1000 hours all animals received the following:
Timolol Group: Normal saline
Timolol/Dexamethasone group: dexamethasone 0.007% (0.01% dexamethasone phosphate)
Saline Control: normal saline.

IOP was then measured at 1030 hours. At 1045 hours the animals received one drop each of the following:
Timolol group: 0.07% timolol (0.1% timolol maleate)
Timolol/Dexamethasone group: 0.07% timolol (0.1% timolol maleate)
Saline Control: normal saline
IOP was then measured every thirty minutes from 1100 hours until 1500 hours.

Figure 9:
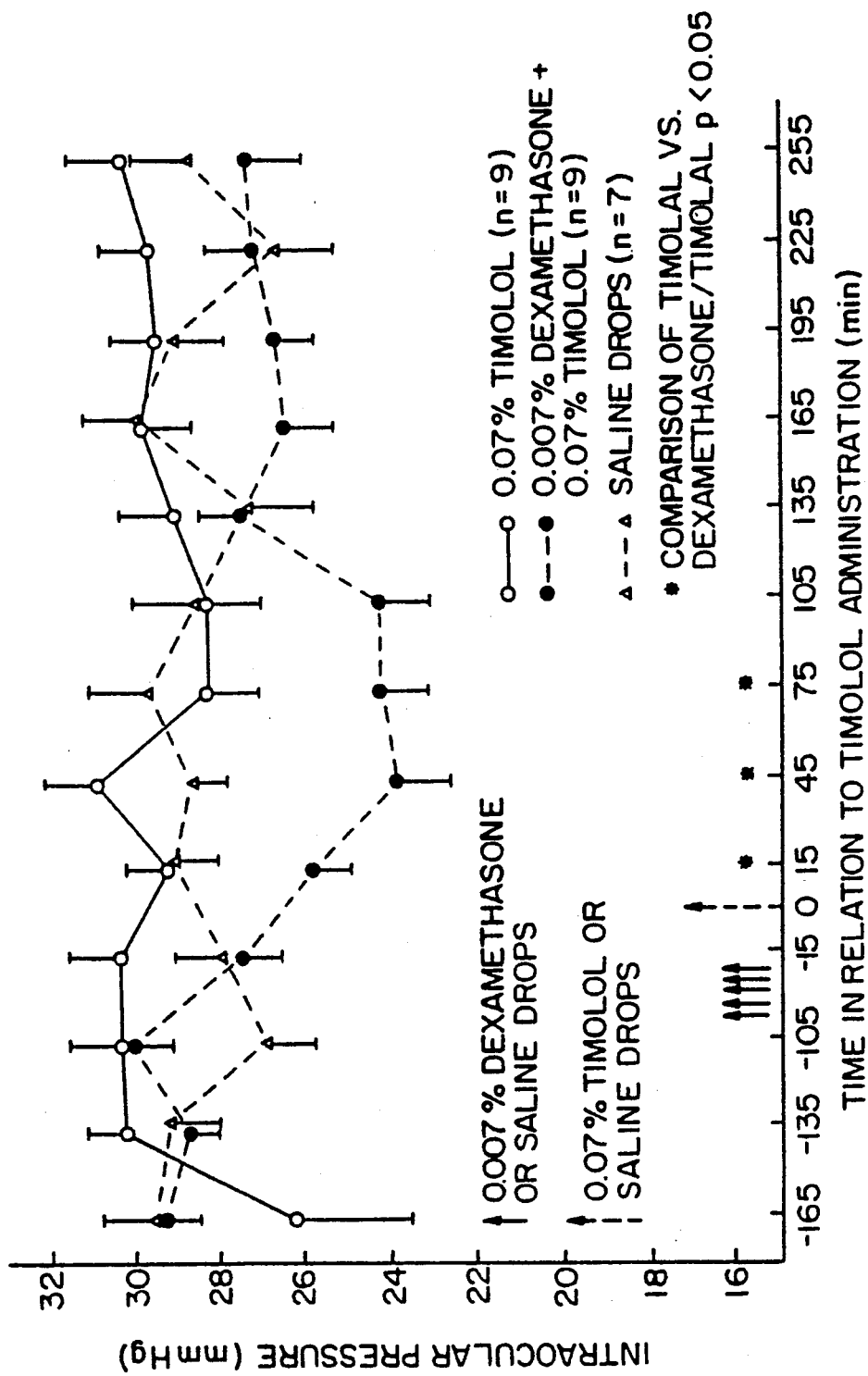
FIG. 9: The mean ± standard error of the mean for intraocular pressure (right eye) response in rabbits to 0.07% timolol (0.1% timolol maleate), 0.07% timolol ±0.007% dexamethasone or saline drops. The vertical bars are the standard errors of the mean. The asterisks indicate the times at which the timolol/dexamethasone group was significantly different from the timolol group. The arrows indicate time of administration of the drops.
Figure 10:
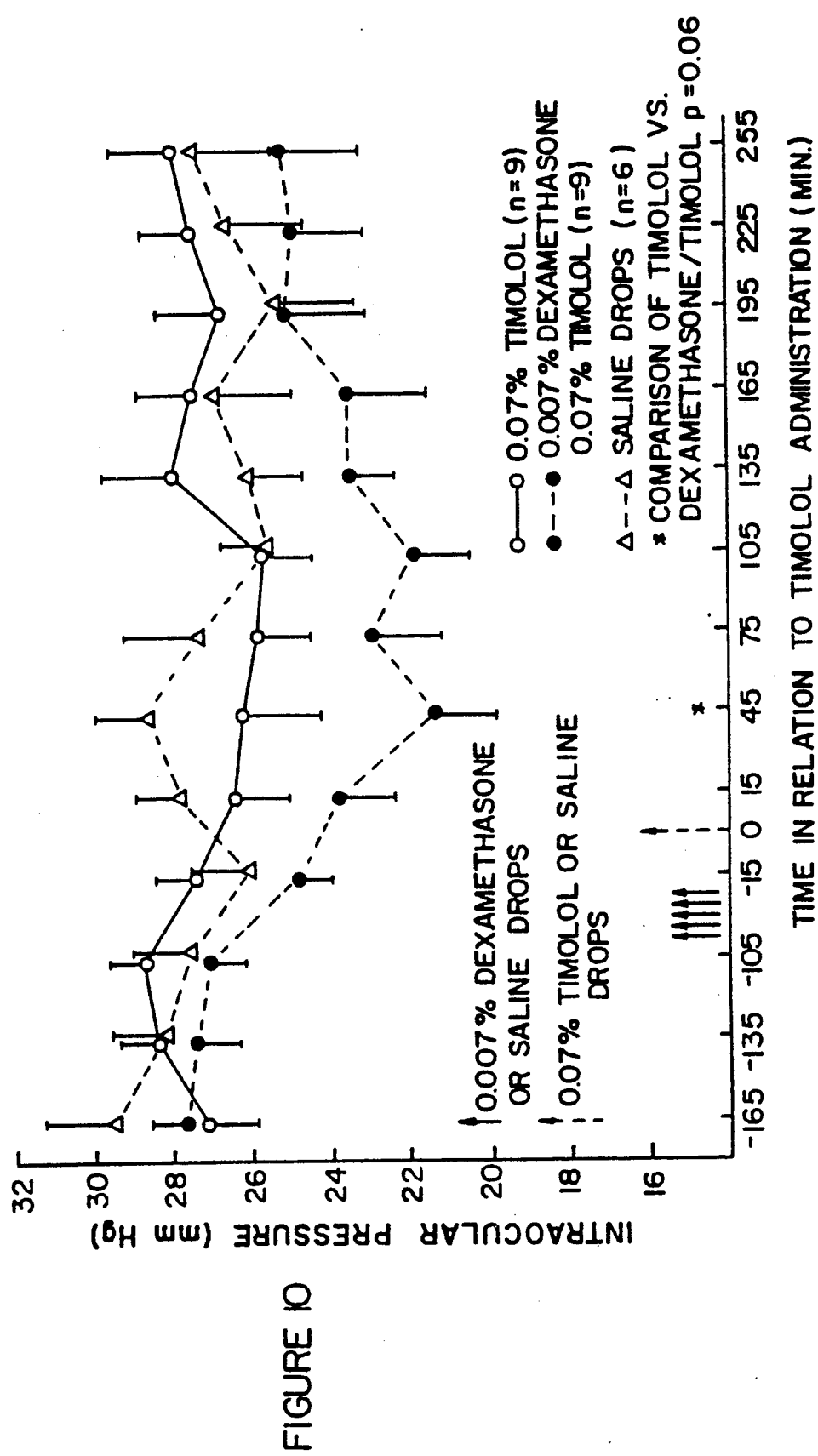
FIG. 10: The mean ± standard error of the mean (left eye for response in rabbits to 0.07% timolol (0.1% timolol mealeate) 0.07% timolol ±0.007% dexamethasone or saline drops. The vertical bars are the standard errors of the mean. The asterisks indicate the times at which the timolol/dexamethasone group was significantly different from the timolol group. The arrows indicate time of administration of the drops.

The results are shown in FIGS. 9 and 10 and Table 4 and demonstrate a significant enhancement of lowering of ocular pressure with dexamethasone plus timolol compared to timolol alone.

TABLE 4

Comparison of saline, Timolol, and Timolol/Dexamethasone groups at 0.07% Timolol (0.1% Timolol Maleate) and 0.007% Dexamethasone (0.01% Dexamethasone Phosphate).

| Time (min**) | Eye (OD/OD) | Saline group mean ± SEM (n*) | Timolol group mean ± SEM (n*) | Timolol/Dexamethasone group mean ± SEM (n*) | p-value*** |
|---|---|---|---|---|---|
| 15 | OD | 29.0 ± 1.0 (7) | 29.1 ± 1.0 (9) | 25.8 ± 0.9 (9) | 0.04 |
| 45 | OD | 28.6 ± 0.9 (7) | 30.9 ± 1.4 (9) | 23.8 ± 1.2 (9) | 0.02 |
| 75 | OD | 29.7 ± 1.4 (7) | 28.2 ± 1.3 (9) | 24.2 ± 1.1 (9) | 0.04 |
| 45 | OS | 28.5 ± 1.4 (6) | 26.2 ± (1.9) (9) | 21.2 ± 1.5 (9) | 0.06 |

*n = number of animals in each group.
**Time is calculated following the administration of Timolol.
***p-value from Mann-Whitney U test-comparison of the Timolol group with dexamethasone/timolol group.

TABLE 5

Comparison of Ocular Pressure of Timolol Treated Eye with Timolol plus Dexamethasone Treated Eye

| Times in relation to drug administration (min) | Ocular Pressure (mmHg) | | Paired t Test p |
|---|---|---|---|
| | Timolol Alone Mean ± SD (No.) | Timolol plus Desamethasone Mean ± SD (No.) | |
| Baseline 1 | 22.6 ± 1.9 (5) | 22.4 ± 1.7 (5) | 0.87 |
| Baseline 2 | 22.6 ± 1.9 (5) | 22.6 ± 1.9 (5) | 1.00 |
| 20 | 21.6 ± 1.7 (5) | 20.6 ± 3.0 (5) | 0.43 |
| 40 | 21.6 ± 1.7 (5) | 18.8 ± 3.0 (5) | 0.11 |
| 60 | 21.8 ± 1.1 (5) | 17.8 ± 2.7 (5) | 0.02 |
| 80 | 21.2 ± 2.3 (5) | 17.6 ± 3.0 (5) | 0.06 |
| 100 | 21.2 ± 1.1 (5) | 17.2 ± 2.3 (5) | 0.008 |

EXAMPLE 5

Enhanced Ocular Hypotensive Response to Timolol and Dexamethasone—an Acute Clinical Trial in Ocular Hypotensives Five patients with untreated ocular hypertension were selected from the outpatient service of the Ophthalmology Department of the New England Medical Center. Informed consent was obtained and the protocol was approved by the Human Investigation Review Committee. These patients had complete ocular examinations to determine that no other significant ocular pathology was present.

On the day of the study, two baseline IOP measurements were taken 10 minutes apart in each eye between 8:00 and 9:00 AM. The study drugs were then administered five minutes apart in the following manner: one eye received three drops of 0.01% dexamethasone phosphate (Decadron phosphate, Merck, Sharp and Dohme, equivalent to 0.007% dexamethasone) diluted with artificial tears (Lacril, Allergan, hydrocypropyl methycellulose with 0.5% chlorobutanol) followed by one drop of 0.01% timolol maleate (Timoptic-Merck, Sharp, Dohme). The other eye received three drops of artificial tears plus one drop of 0.01% timolol maleate. After drug administration, ocular pressures were taken every twenty minutes for two hours.

Dexamethasone phosphate and artificial tear drops were prepared by the hospital pharmacist who placed each solution in identical containers labeled with codes. The pharmacist prepared a random series for the choice of eye for dexamethasone or artificial tears. The code was broken at the end of the series.

Figure 11:
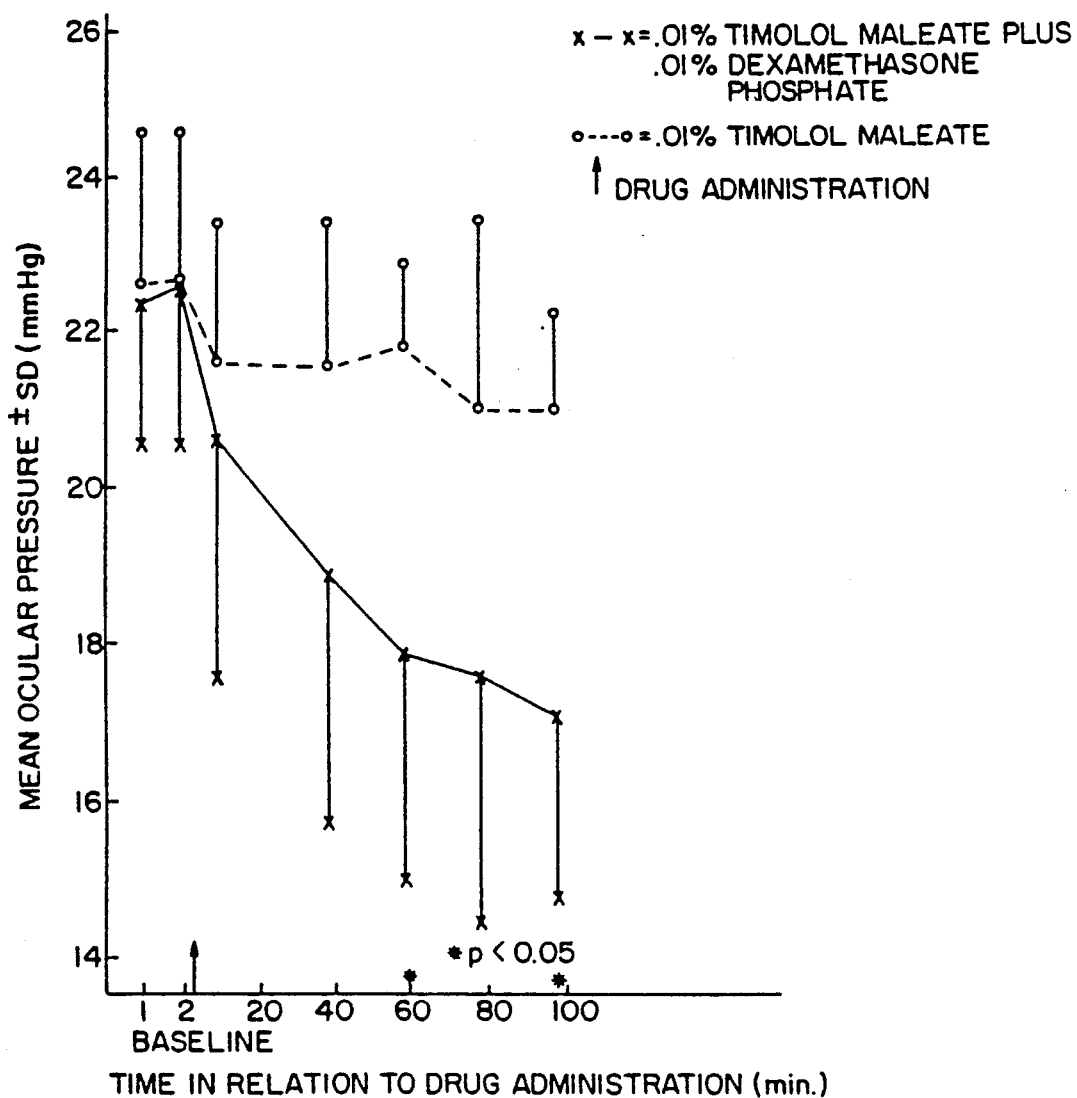
FIG. 11: The mean ± standard deviation of intraocular response in human eyes to 0.01% timolol maleate and 0.01% dexamethasone phosphate plus 0.01% timolol maleate. The vertical bars represent standard deviations from the mean. The arrow represents time of timolol administered. The asterisks represent time intervals where the intraocular pressure differences are significant ($p < 0.05$).

The results are shown in FIG. 11 and Table 5 and demonstrate that dexamethasone plus timolol were more effective in lowering ocular pressure in human eyes than timolol alone. Furthermore, the doses used were much less than those commonly used in clinical practice.

Apraclonidine hydrochloride, an alpha adrenergic agent, when administered in a concentration range of about 0.1% to 0.25% with one of the aforementioned corticosteriods in their preferred concentration form will likewise more effectively lower intraocular pressure at lower dosage and will be more effective and suitable for chronic use than apraclonidine hydrochloride used above, based on the data shown herein for the alpha and beta adrenergic agents.

What is claimed is:

1. A method for treating elevated intraocular pressure in a mammalian eye comprising:
   administering to the eye a therapeutically effective amount of a corticosteroid and an alpha adrenergic agent;
   said corticosteroid selected from the group consisting of dexamethasone having a concentration from 0.0005 to 0.01%, prednisolone having a concentration from 0.0005% to 0.1%, hydrocortisone having a concentration from 0.0025 to 0.05%, cortisone having a concentration from 0.0125 to 0.25%, fluorometholone having a concentration from 0.0005 to 0.01%, betamethasone having a concentration from 0.0005 to 0.01%, methyl prednisolone having a concentration from 0.04 to 0.8%, triamcinolone having a concentration of 0.0005 to 0.01%, and their physiologically acceptable salts;
   said alpha adrenergic agent being apraclonidine hydrochloride having a concentration ranging from about 0.1% to 0.25% and its physiologically acceptable salts;
   the concentration of said corticosteroid and said alpha adrenergic agent being selected to produce a prolonged decrease in intraocular pressure while minimizing undesirable side effects of said corticosteroid and said alpha adrenergic agent.

2. The method of claim 1 wherein said corticosteroid and said alpha adrenergic agent are applied in combination.

3. The method of claim 1 wherein said corticosteroid and said alpha adrenergic agent are applied in sequence.

4. The method of claim 3 wherein the corticosteroid is administered systemically.

5. A solution for treating elevated intraocular pressure in a mammalian eye comprising:

a corticosteroid selected from the group consisting of dexamethasone having a concentration from 0.0005 to 0.01%, prednisolone having a concentration from 0.005 to 0.1%, hydrocortisone having a concentration from 0.0025 to 0.05%, cortisone having a concentration from 0.0125 to 0.25%, fluorometholone having a concentration from 0.0005 to 0.01%, betamethasone having a concentration from 0.0005 to 0.01%, methyl prednisolone having a concentration from 0.04 to 0.8%, triamcinolone having a concentration of 0.0005 to 0.01% and their physiologically acceptable salts;

an alpha adrenergic agent being apraclonidine hydrochloride having a concentration ranging from about 0.1% to 0.25% and its physiologically acceptable salts;

the concentration of said corticosteroid and said alpha adrenergic agent being selected to produce a prolonged decrease in intraocular pressure while minimizing undesirable side effects of said corticosteroid and said alpha adrenergic agent.

* * * * *